(12) United States Patent
Shan

(10) Patent No.: US 9,801,606 B2
(45) Date of Patent: Oct. 31, 2017

(54) STETHOSCOPE HEAD WITH ADJUSTABLE AUDIO FREQUENCY

(76) Inventor: Xijie Shan, Wuxi (CN)

(*) Notice: Subject to any disclaimer, the term of this patent is extended or adjusted under 35 U.S.C. 154(b) by 640 days.

(21) Appl. No.: 13/640,039

(22) PCT Filed: Sep. 6, 2010

(86) PCT No.: PCT/CN2010/001352
§ 371 (c)(1),
(2), (4) Date: Oct. 8, 2012

(87) PCT Pub. No.: WO2011/127633
PCT Pub. Date: Oct. 20, 2011

(65) Prior Publication Data
US 2013/0041287 A1    Feb. 14, 2013

(30) Foreign Application Priority Data
Apr. 16, 2010 (CN) .......................... 2010 1 0153009
Apr. 16, 2010 (CN) ...................... 2010 2 0165472 U

(51) Int. Cl.
*A61B 7/02* (2006.01)
*A61B 7/04* (2006.01)

(52) U.S. Cl.
CPC . *A61B 7/02* (2013.01); *A61B 7/04* (2013.01)

(58) Field of Classification Search
CPC .................................... A61B 7/02; A61B 7/04
USPC ................................................ 181/131, 137
See application file for complete search history.

(56) References Cited

U.S. PATENT DOCUMENTS

| 3,157,246 | A | * | 11/1964 | Howell | 181/137 |
| 4,012,604 | A | * | 3/1977 | Speidel | 367/180 |
| 4,903,794 | A | * | 2/1990 | Klippert et al. | 181/131 |
| 5,389,747 | A | * | 2/1995 | Mohrin | 181/131 |
| 5,832,093 | A | * | 11/1998 | Bernstein | A61B 7/04 381/67 |
| 6,244,376 | B1 | | 6/2001 | Granzotto | |
| 6,499,560 | B1 | | 12/2002 | Lang | |

FOREIGN PATENT DOCUMENTS

| CN | 2862968 Y | | 1/2007 |
| CN | 1923142 | * | 3/2007 |
| CN | 101091658 A | | 12/2007 |
| CN | 101647712 A | | 2/2010 |
| CN | 201409934 Y | | 2/2010 |

* cited by examiner

Primary Examiner — Matthew Kremer
(74) Attorney, Agent, or Firm — Han IP Corp; Andy Han

(57) ABSTRACT

A stethoscope head with adjustable audio frequency includes a head body, a diaphragm and a fastener. The diaphragm includes an annular step and a footing, and is disposed on a sound collecting surface on a front side of the head body and fixed on the head body by the fastener. An outer marginal part of a front side of the head body is provided with the annular step, and screw threads are provided on a step surface of the annular step. An annular groove is provided at the sound collecting surface inside the annular step. The inner surface of the annular groove and the bottom surface of annular recess form an obtuse angle γ. The diaphragm footing is disposed in the annular groove. The stethoscope head of the invention is convenient to assemble and the sound effect can be adjusted continuously.

15 Claims, 7 Drawing Sheets

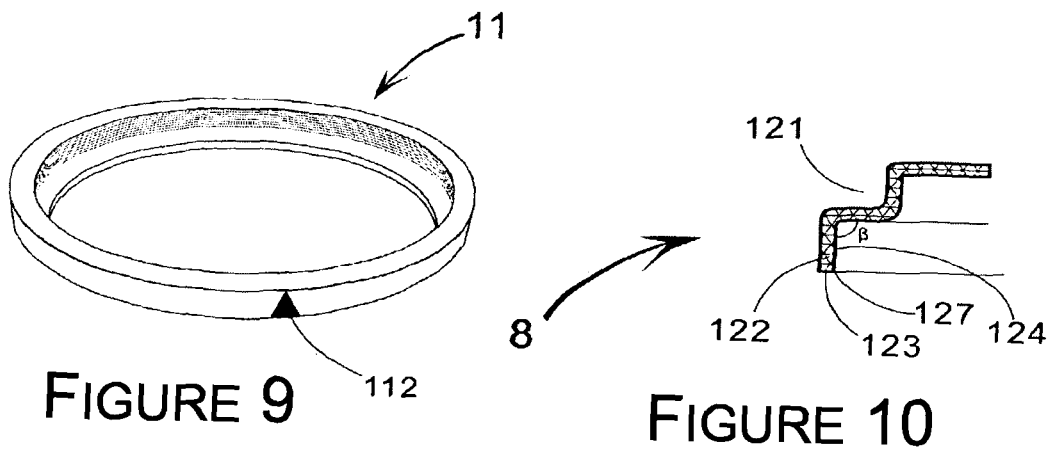
FIGURE 9
FIGURE 10
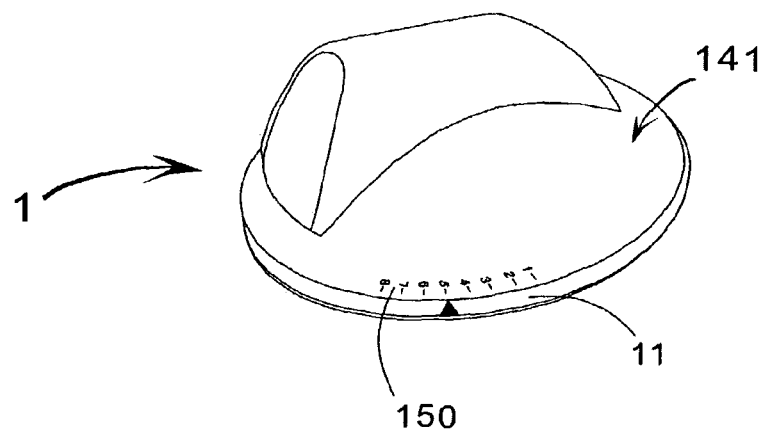
FIGURE 11

STETHOSCOPE HEAD WITH ADJUSTABLE AUDIO FREQUENCY

CROSS-REFERENCE TO RELATED APPLICATION

This application is the national phase application of international application number PCT/CN2010/001352, filed on Sep. 6, 2010, which claims the priority benefit of China Patent Application No. 201020165472.X, filed on Apr. 16, 2010, and China Patent Application No. 201010153009.8, filed on Apr. 16, 2010. The above-identified applications are incorporated by reference in their entirety.

TECHNICAL FIELD

The invention relates to a medical equipment assembly and, more particularly, to a stethoscope assembly.

BACKGROUND

As shown in FIG. 1, a conventional stethoscope includes a head 1, a rubber tube 2, ear tubes 3 and earpieces 4. When a user listens to multiple sounds with different audio frequencies, he or she usually needs to change the volume of a sound collecting chamber of the head 1. Namely, the user can change the volume of the sound collecting chamber when he or she needs to listen to both a high frequency sound and a low frequency sound.

As shown in FIG. 2 and FIG. 3, in the conventional stethoscope, a diaphragm 12 is disposed at a head body 14 and is fastened via a fastener 11. The fastener 11 is an annular rubber ring and wraps an annular step 121 of the diaphragm 12 and the head body 14 to fasten the diaphragm 12 to the head body 14.

When the conventional stethoscope is used, if the user would like to switch the listening frequency from a low frequency sound to a high frequency sound, he or she only needs to press the diaphragm 12 to make the diaphragm 12 contact the annular protrusion 145. At that moment, a $\lambda$ angle of the diaphragm changes. However, since a lower surface 128 of the annular step is fastened to a platform 149 of the head body by the fastener 11, it is difficult to change the $\lambda$ angle. The user needs to spend more effort to press the head body 14 to change the $\lambda$ angle. As the result, the user may feel uncomfortable.

Furthermore, every user has his or her own audibility, preference and auscultation habit, but he or she cannot adjust the sound intensity of the conventional stethoscope, and can only use the predetermined frequency.

Furthermore, the conventional dual-frequency stethoscope head is not convenient to assemble, and it needs a skilled person to assemble carefully to ensure the hearing effect.

Moreover, if the hearing effect is reduced due to deviation during the operation process, the user cannot adjust the hearing effect by himself or herself.

SUMMARY

An object of the invention is to provide a stethoscope head in which the assembling is easy, the sound effect is adjustable, sounds with different sound intensities can be heard, and can be adjusted continuously.

To solve the problem above, the invention provides a stethoscope head with adjustable audio frequency including a head body, a diaphragm and a fastener. The diaphragm is provided with an annular step and a footing. The diaphragm is disposed on a sound collecting surface at the front side of the head body and is fastened to the head body by the fastener. The outer marginal part of the front side of the head body is provided with the annular step, and a screw thread is provided on a step surface of the annular step. An annular recess is provided at the sound collecting surface at the inner side surface of the annular step, and the inner side surface of the annular recess and the bottom surface of the annular recess form an obtuse angle $\gamma$, and $100° \leq \gamma \leq 145°$. The diaphragm footing is disposed in the annular recess and contacts the inner side surface of the annular recess. The fastener includes a ring A and a ring B whose upper surfaces are located at the same horizontal plane. The ring B is place in the ring A and the external diameter of the ring B is the same as the internal diameter of the ring A. An inner wall of the ring A is provided with a screw thread which matches with the screw thread on the step surface. The screw pitches of the two matching screw threads are small pitch which ranges from 0.25 mm to 0.75 mm. This is benefit for improving the accuracy of the audio frequency.

Since the $\gamma$ angle is an obtuse angle, when a downward force is applied to the diaphragm, the force is decomposed of a horizontal force and a vertical force when applied to the inner side surface of the annular recess. As a result, the upward reacting force applied to the diaphragm is the vertical force provided by the inner side surface of the annular recess. The horizontal reacting force applied to the diaphragm is the horizontal force provided by the inner side surface of the annular recess, and the force changes the $\beta$ angle between the diaphragm footing and the annular step. The contacting surfaces between the diaphragm and the annular recess of the head body are the bottom surface of the diaphragm and the inner side surface of the footing of the diaphragm. The diameter of the transverse section of the annular recess increases from top to bottom. When the diaphragm is pressed downwardly, the $\beta$ angle increases, the diaphragm footing moves downwardly along the inner side surface of the annular recess. As a result, the sound leakage between the diaphragm and the contacting surfaces of the head body during switching the audio frequency can be avoided.

The more the $\gamma$ angle is approximated to a right angle, the less the upward reacting force exerted to the diaphragm is, and the larger the horizontal reacting force is. As a result, the Bangle is easy to increase, and the diaphragm is easier to be pressed downwardly. However, when the $\gamma$ angle increases, the upward reacting force applied to the diaphragm increases too, and the horizontal reacting force reduces therewith. The $\beta$ angle is difficult to increase, and the user needs to spend more effort to press the diaphragm downwardly. However, the more the $\gamma$ angle is approximated to a right angle, the more difficult the diaphragm moves back to the original position after switching the frequency band due to the exerted upward force is less.

Furthermore, the sound collecting surface at the inner side of the annular recess is provided with an annular protrusion, and a washer is disposed on the annular protrusion or a recess is disposed at the annular protrusion. The recess is also provided with a washer, and the washer can improve the sealing ability of the sound collecting chamber to achieve better listening effect.

Furthermore, a sealing ring is disposed between the annular step and the ring A, and the sealing ring can avoid the sound leakage between the bottom surface of the ring A of the fastener and the contacting surface of the annular step when listening to a low frequency sound. The sealing ring has high elasticity, and it exerts a reacting force to the ring of the fastener 11 when the lower surface of the fastener 11 is pressed. The stableness during usage is achieved by improving the uneasy-to-shift ability when a non-initiative force is applied to the fastener 11, and the uneasy-to-shift ability is achieved by increasing the friction force between the inner screw thread of the ring and the screw thread of the step surface of the annular ring.

Furthermore, the back side of the head body is provided with graduation, and the outer surface of the ring A is provided with an arrow. When the fastener moves non-initiatively and makes the listening effect change, the user can memory the graduation that is directed by the arrow to restore the original position, and he or she does not needs to spend much effort to adjust the listening effect.

The invention has advantages hereinbelow:

1. The conventional stethoscope provides only audio frequencies in two fixed bands, but the stethoscope in the invention can provide frequencies in two main bands and frequencies in multiple secondary bands. The user can adjust the crisp of the frequency according to his or her auscultation habit.

2. The conventional stethoscope requires high skill in assembling and changing components, and it need skilled persons to assemble. During the assembling, it is easy to lose the dual-frequency function unintentionally. However, the stethoscope in the invention is easy to assemble, and the assembling process does not need the help of skilled persons. The multi-frequency function can be achieved after simple assembling process.

3. In the conventional technology, a larger pressure needs to be applied to the stethoscope to achieve a dual-frequency effect, and the pressure force is usually 9.23N to 11.12N. In the invention, the same frequency effect can be obtained by applying only 5.39N to 7.23 N pressure force.

4. In the conventional technology, the diaphragm is easy to get fatigue, and generally it can be used for 25000 to 30000 times. In the invention, the diaphragm is not easy to get fatigue, and generally it can be used form 50000 to 60000 times.

5. In the conventional technology, if the audio frequency has deviation and the listening effect is reduced, user is not capable of adjusting the listening effect. In the invention, if the sound frequency has deviation and the listening effect is reduced, the user can adjust and repair the stethoscope by himself or herself.

BRIEF DESCRIPTION OF THE DRAWINGS

FIG. 9 is a schematic diagram showing the fastener in an embodiment of the invention.

FIG. 10 is a partial diagram showing the diaphragm 12 in FIG. 4.

FIG. 11 is a back view of the stethoscope head in an embodiment of the invention.

Figure 1:
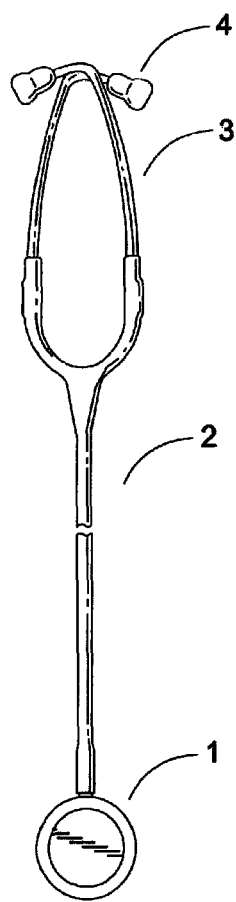
FIG. 1 is a schematic diagram showing a conventional stethoscope.
Figure 2:
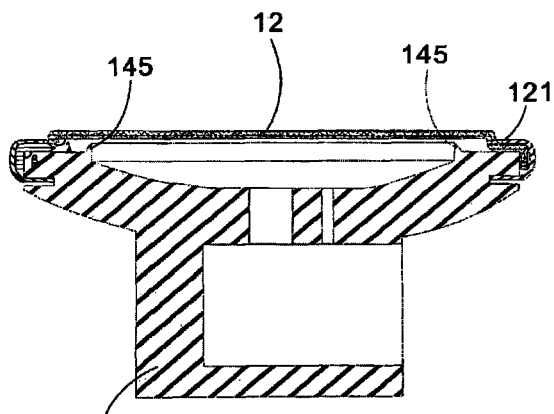
FIG. 2 is a schematic diagram showing a stethoscope head in the conventional stethoscope.
Figure 3:
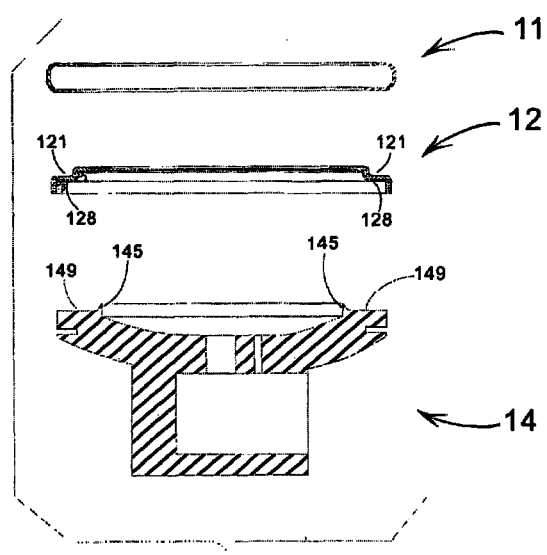
FIG. 3 is an exploded diagram of FIG. 2.
Figure 4:
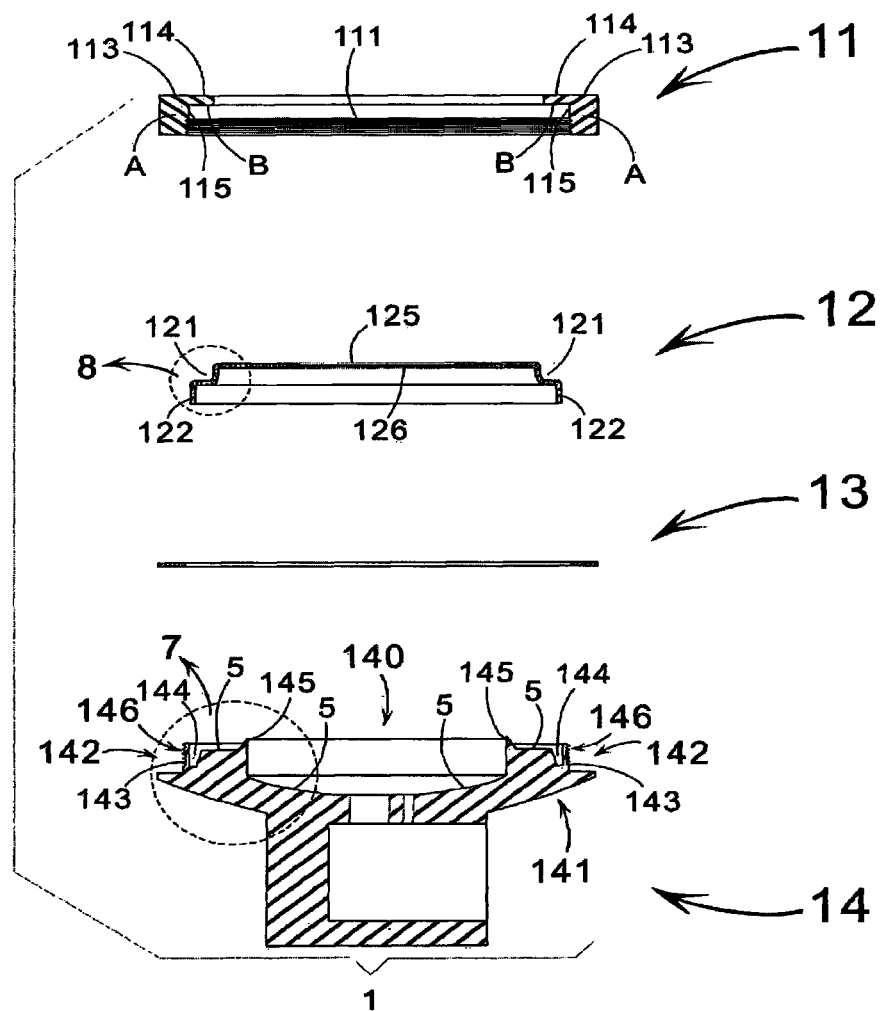
FIG. 4 is an exploded diagram showing a stethoscope head in an embodiment of the invention.
Figure 5:
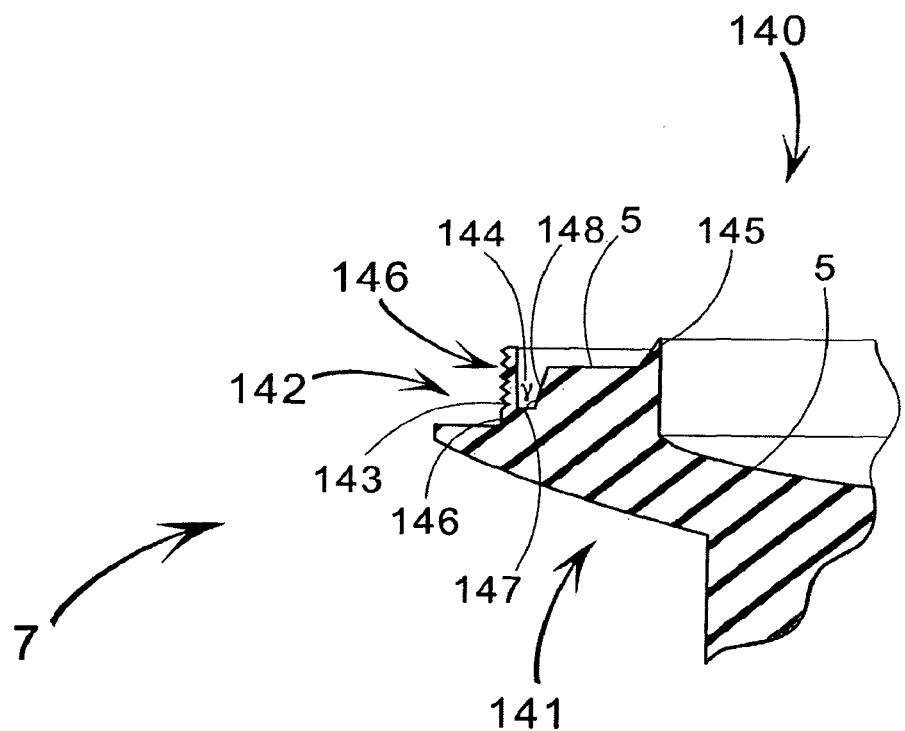
FIG. 5 is an enlarged schematic diagram showing a section in the head body 14 in FIG. 4.

NUMERAL REFERENCES OF ELEMENTS 1 head body; 2 rubber tube; 3 ear tube; 4 ear piece; 5 sound collecting surface; 6 sound collecting chamber; 11 fastener; 111 screw thread; 112 arrow; 113 upper surface of ring A; 114 upper surface of ring B; 115 inner surface of ring A; 116 bottom surface of ring A; 12 diaphragm; 121 annular step of diaphragm; 122 diaphragm footing; 123 bottom surface of diaphragm; 124 inner surface of diaphragm footing; 125 upper surface of diaphragm; 126 lower surface of diaphragm; 127 bottom edge of the inner surface of the diaphragm footing; 128 lower surface of annular step; 13 sealing ring; 14 head body; 140 front side of head body; 141 back side of head body; 142 annular step; 143 screw thread; 144 annular recess; 145 annular protrusion; 146 step surface; 147 bottom surface; 148 inner side surface; 149 platform; 150 graduation; 160 washer; 1451 recess.

DETAILED DESCRIPTION OF THE PREFERRED EMBODIMENTS

Hereinafter, the embodiments are described in details along with the accompanying drawing. Hereinafter, several the embodiments are illustrated with the accompanying drawings.

Embodiment 1

Embodiment 1 is illustrated along with FIG. 4, FIG. 5, FIG. 6, FIG. 7, FIG. 9 and FIG. 10.

A stethoscope head with adjustable audio frequency includes a head body 14, a diaphragm 12 and a fastener 11. The outer marginal part of the front side 140 of the head body is provided with an annular step 142, and a step surface 146 of the annular step 142 is provided with a screw thread. A sound collecting surface 5 at the inner side of the annular step 142 is provided with an annular recess 144, and an inner side surface 148 and a bottom surface 147 of the annular recess 144 form an obtuse angle γ.

The fastener 11 includes a ring A and a ring B, an upper surface 113 of the ring A and an upper surface 114 of the ring B are in the same horizontal plane. The ring B is disposed inside the ring A and the external diameter of the ring B is the same as the internal diameter of the ring A. The inner wall 115 of the ring A is provided with a screw thread 111 to match with the screw thread 143 of the step surface.

The diaphragm 12 is provided with an annular step 121 and a footing 122. The footing 122 of the diaphragm 12 is disposed in the annular recess 144. The bottom surface 127 of the inner surface of the footing 122 of the diaphragm 12 contacts the inner side surface 148 of the annular recess 144, and the diaphragm 12 is fastened to the head body 14 via the fastener 11.

The inner side surface 148 and the bottom surface 147 of the annular recess 144 form an obtuse angle γ, and 100°≤γ≤145°.

Embodiment 2

As shown in embodiment 1 and combining with FIG. 4, FIG. 6, FIG. 7, FIG. 9 and FIG. 10, an annular protrusion 145 is further disposed on the sound collecting surface 5 at the inner side of the annular recess 144.

The inner side surface 148 of the annular recess 144 and the bottom surface 147 of the annular recess form an obtuse angle γ, and 100°≤γ≤145°.

Figure 13:
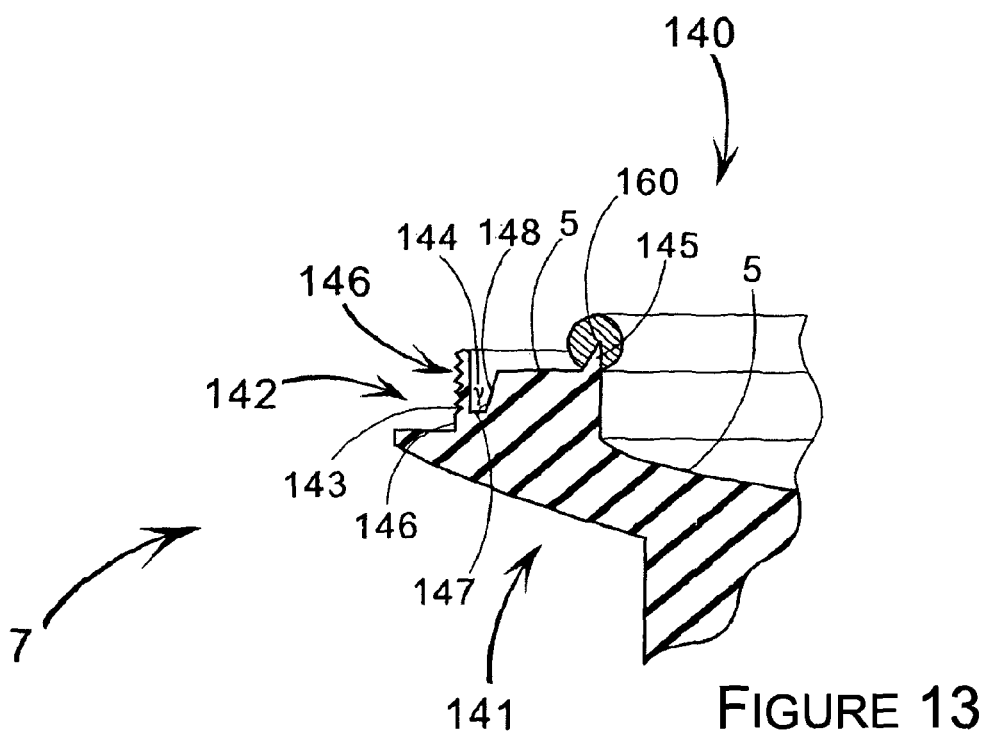
FIG. 13 is a first partial diagram showing the annular protrusion 145 of the head body 14 and the washer 160 disposed on the annular protrusion 145.

Combining with the above drawings and FIG. 13, a washer 160 is further provided on the annular protrusion 145. Adding the washer 160 can improve the sealing ability of the sound collecting chamber and improve the sound effect.

Figure 6:
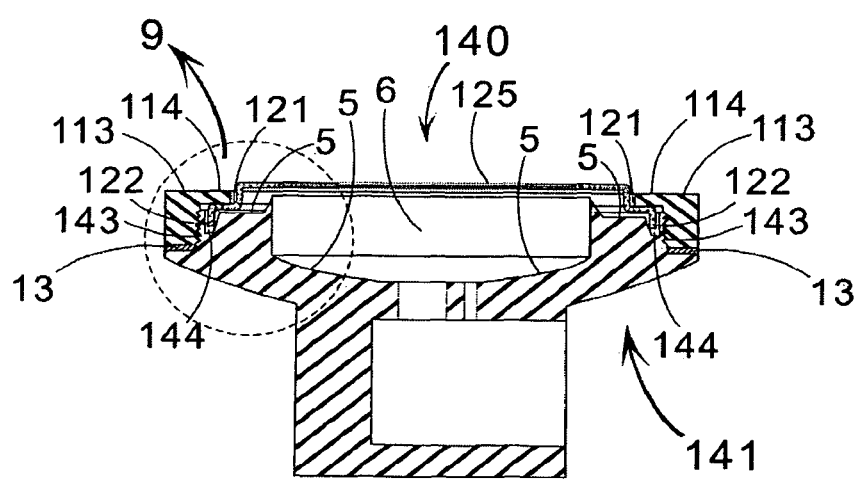
FIG. 6 is a first schematic diagram showing the stethoscope head in an embodiment of the invention.
Figure 7:
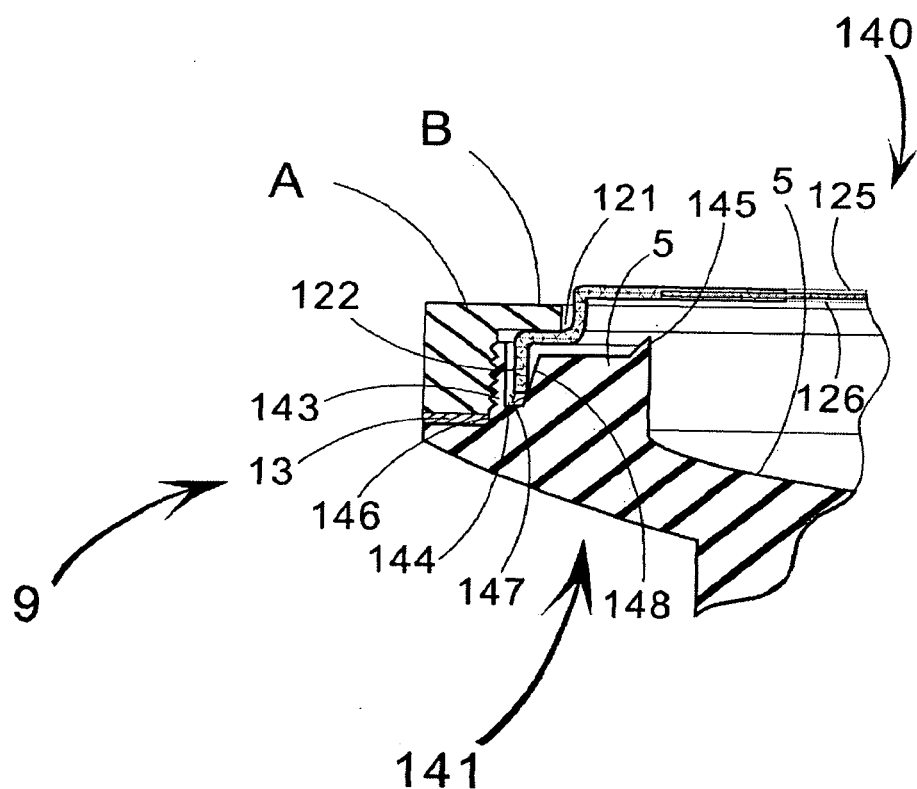
FIG. 7 is an enlarged schematic diagram showing a section of the head body 14 in FIG. 6.
Figure 8:
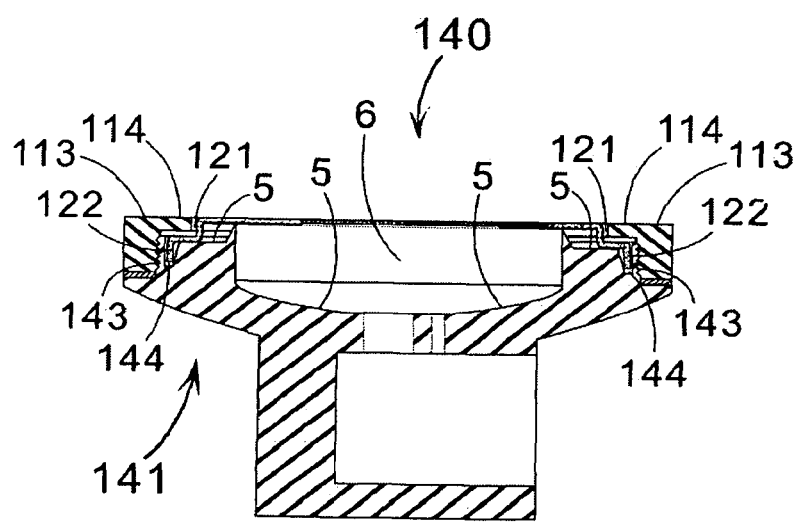
FIG. 8 is a second schematic diagram showing the stethoscope head in an embodiment of the invention.

Combining with the above drawings and FIG. 6 and FIG. 7, when a low frequency is listened, the user only needs to contact the upper surface 125 of the diaphragm 12 to the auscultation object. Combining with FIG. 8, if a high frequency is listened, the user only needs to press the head body 14 to make the diaphragm footing 122 move downwardly in the annular recess 144 until the lower surface 126 of the diaphragm butts the annular protrusion 145.

| γ angle (degree) | The required pressure which makes the lower surface 126 of the diaphragm contact the annular protrusion 145, (namely obtaining another audio frequency) (N) | Stethoscope attenuation value under 500 HZ frequency and 114 DB sound source (DB) | Stethoscope attenuation value under 750 HZ frequency and 114 DB sound source (DB) |
| --- | --- | --- | --- |
| 100 | 3.95 | 7.82 | 6.95 |
| 110 | 5.03 | 5.01 | 4.23 |
| 120 | 5.39 | 5.23 | 4.18 |
| 130 | 7.85 | 6.32 | 5.23 |
| 140 | 9.23 | 6.98 | 5.64 |
| 145 | 10.37 | 7.81 | 7.12 |
| 150 | 12.85 | 8.32 | 7.26 |
| 160 | 15.32 | 8.76 | 8.12 |

It is concluded from the above data that:

Firstly, considering obtaining good frequency change effect and the auscultation area is not uncomfortable due to pressure, the less the γ angle between the inner side surface 148 of the annular recess 144 and the bottom surface 147 of the annular recess 144 is, the pressure that makes the lower surface 126 of the diaphragm contact the annular protrusion 145 (namely the required pressure for obtaining another audio frequency) is less. However, in practical auscultation, if the pressure is too small, during obtaining the other audio frequency, the upper surface 125 of the diaphragm does not totally contact the auscultation area, which affects the auscultation. The general proper pressure for changing the frequency is larger than 5N and less than 10N. Under proper pressure scope, the stethoscope can obtain preferable frequency-change effect and the auscultation area is not easy to be uncomfortable due to pressure.

Secondly, considering frequency attenuation, the angle γ formed between the inner side surface 148 of the annular recess 144 and the bottom surface 147 of the annular recess ranges above or equal to 100° and less than 145°. The audio frequency attenuation is less.

Thirdly, considering both the audio frequency attenuation and the effectiveness of auscultation, the angle γ formed between the inner side surface 148 of the annular recess 144 and the bottom surface 147 of the annular recess is preferable above or equal to 100° and less than 145°

Fourthly, the thickness of the diaphragm footing 0.6 mm, and the hardness of the rubber is 60° shore hardness.

The elasticity is measured in the method and parameter hereinbelow: the upper surface of a square rubber block is applied by 19.6 N vertical force, and the downward and vertical deformation distance is 1.21 mm.

Figure 12:
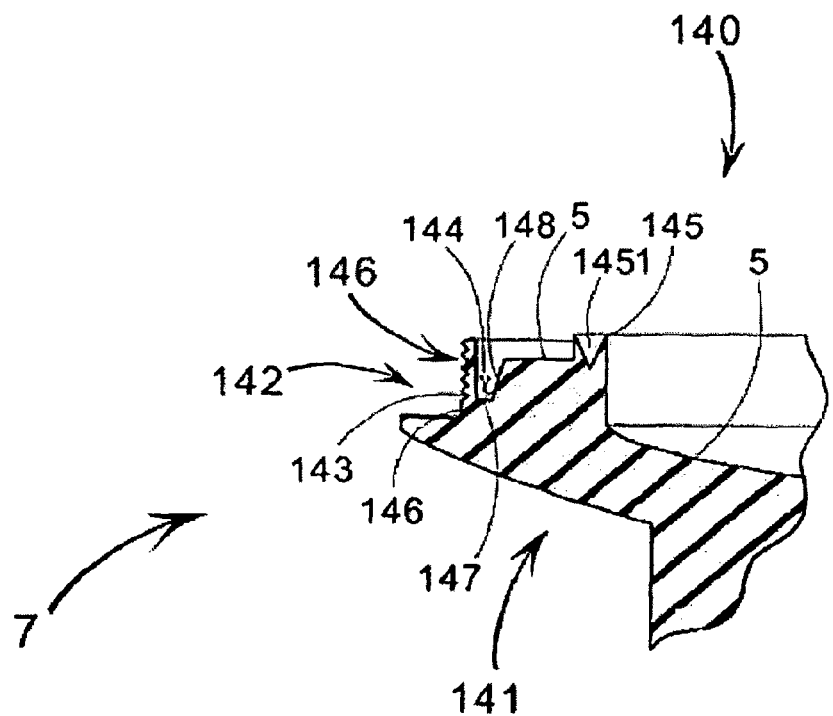
FIG. 12 is a partial diagram showing the annular protrusion 145 of the head body 14 and the annular recess 1451 disposed on the annular protrusion 145.
Figure 14:
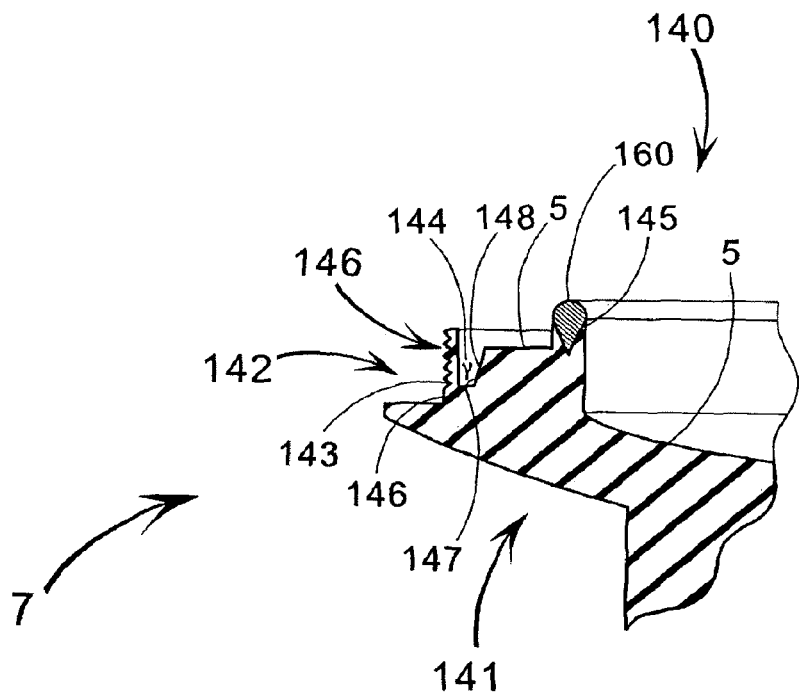
FIG. 14 is a second partial diagram showing the annular protrusion 145 of the head body 14 and the washer 160 disposed on the annular protrusion 145.
Figure 15:
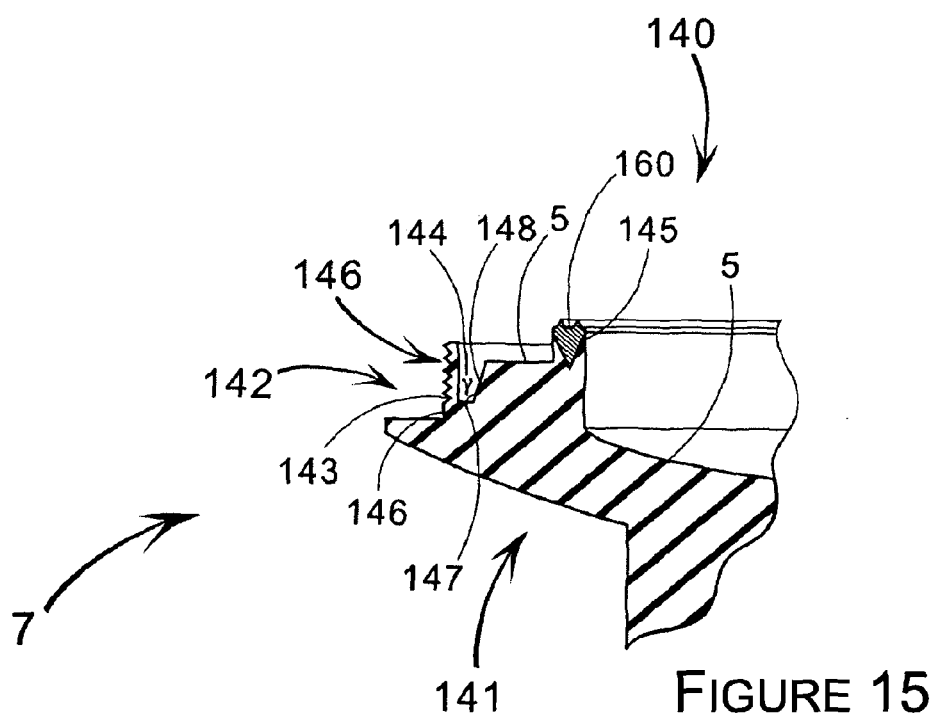
FIG. 15 is a third partial diagram showing the annular protrusion 145 of the head body 14 and the washer 160 disposed on the annular protrusion 145.

Combining with FIG. 12, the annular protrusion 145 is also provided with an annular recess 1451, and the annular recess 1451 is disposed on the annular protrusion 145 to make the amount of the surface butting the lower surface 126 of the diaphragm increased to two annular surfaces. As a result, the sealing effect of the sound collecting chamber is improved, and the preferable listening effect is achieved. Combining with FIG. 14, a washer 160 is further disposed in the recess of the annular recess 1451, and when the head body 14 is pressed, the diaphragm footing 122 moves downwardly in the annular recess 144 until the lower surface 126 of the diaphragm butts the washer 160 of the annular protrusion 145. As a result, the sealing effect is improved, and the preferable listening effect is achieved. Combining with FIG. 15, the washer 160 is provided with two annular edges, when the head body 14 is pressed, the two annular edges butt the lower surface 126 of the diaphragm and form the sound collecting chamber 6. The contacting surfaces of the washer 160 and the lower surface 126 of the diaphragm are increased, the sealing effect of the sound collecting chamber 6 is improved, and the listening effect is better. The shape of each of the two annular edges of the washer 160 may be triangle, semi-circle and so on.

Embodiment 3

As shown in embodiment 1 and combining with FIG. 4, FIG. 6, FIG. 7, FIG. 8, FIG. 9 and FIG. 10, a sealing ring 13 is disposed between the annular step 142 and the ring A. The sealing ring 13 can avoid the sound leakage between the bottom surface 116 of the ring A of the fastener 11 and the contacting surface of the annular step 142 when listening to a low frequency sound. The sealing ring has high elasticity, and it exerts a reacting force to the ring of the fastener 11 when the lower surface of the fastener 11 is pressed. The stableness during usage is achieved by improving the uneasy-to-shift ability when a non-initiative force is applied to the fastener 11, and the uneasy-to-shift ability is achieved by increasing the friction force between the inner screw thread of the ring and the screw thread of the step surface of the annular ring.

Embodiment 4

As shown in embodiment 1, embodiment 2 or embodiment 3, and combining with FIG. 11, the back side 141 of the head body is provided with graduation 150, and the outer surface of the ring A is provided with an arrow 112.

When the fastener 11 moves non-initiatively and makes the listening effect change, the user can memory the graduation that is directed by the arrow to restore the original position, and he or she does not needs to spend much effort to adjust the listening effect.

To sum up, by rotating the fastener 11, the position of the diaphragm can be changed upwardly and downwardly, and tension is generated at the diaphragm footing. Due to the reacting force, the upward elasticity of the footing 122 is increased and the elasticity of the diaphragm is increased, too. As a result, the wave length of the received audio frequency and is changed, thereby achieving the object of adjusting the audio frequency. The volume of the sound collecting chamber is changed, too, and the audio frequency changes therewith to achieve the function of adjusting the audio frequency.

Although the invention has been described as above in reference to several typical embodiments, it is to be understood that the terms used therein are just illustrative and exemplary rather than restrictive. Since the invention can be applied in various forms without departing from the spirit or principle of the invention, it is to be understood that the abovementioned embodiments will not be limited to any specific details mentioned above; rather, they should be construed broadly in the spirit or concept of the invention defined by the appended claims. Therefore, the present invention aims to cover all the modifications or variations falling within the protection scope defined by the appended claims.

What is claimed is:

1. A stethoscope head with an adjustable audio frequency, comprising:
   a head body having an annular step and a sound collecting surface at a front side of the head body, an annular recess being provided on the sound collecting surface and formed in part by an inner side of a step surface of the annular step of the head body;
   an annular fastener having an inner wall and screw threads provided on the inner wall; and
   a diaphragm having an annular step and a footing, the diaphragm disposed on the sound collecting surface of the head body by the annular fastener, the footing of the diaphragm being disposed in the annular recess and directly contacting with the annular recess at an annular circumference,
   wherein the diaphragm is movable relative to the head body,
   wherein a position of the diaphragm relative to the head body is configured to change as the annular fastener is rotated along the screw threads, and
   wherein, when the stethoscope head is in operation, the annular circumference is configured to move along an inner side surface of the annular recess in response to a change in the position of the diaphragm to regulate the audio frequency received by the diaphragm.

2. The stethoscope head of claim 1, wherein the inner side surface of the annular recess and a bottom surface of the annular recess form an obtuse angle $\gamma$ such that the footing of the diaphragm is deformed due to a change in an angle between the footing and the annular step of the diaphragm when a downward force is applied to the diaphragm to change the position thereof.

3. The stethoscope head of claim 2, wherein a range of the obtuse angle $\gamma$ is $100° \leq \gamma \leq 145°$.

4. The stethoscope head of claim 1, wherein the annular step of the head body is disposed at an outer marginal part of the front side of the head body.

5. The stethoscope head of claim 4, wherein a sealing ring is disposed between the annular step of the head body and the annular fastener.

6. The stethoscope head of claim 1, wherein the footing of the diaphragm comprises an elastic material.

7. The stethoscope head of claim 1, wherein the annular fastener comprises an L-shaped cross section, and wherein the step surface of the annular step of the head body is provided with screw threads matching with the screw threads on the inner wall of the annular fastener.

8. The stethoscope head of claim 7, wherein the annular step of the diaphragm abuts against the annular fastener.

9. The stethoscope head of claim 1, wherein an annular protrusion is provided on the sound collecting surface such that when the diaphragm is pressed, a lower surface of the diaphragm contacts the annular protrusion to change the audio frequency received by the diaphragm.

10. A stethoscope head with an adjustable audio frequency, comprising:
    a head body having an annular step and a sound collecting surface at a front side of the head body, the sound collecting surface having an annular protrusion;
    an annular fastener having an inner wall and screw threads provided on the inner wall; and
    a diaphragm having an annular step and a footing, the diaphragm disposed on the sound collecting surface of the head by the annular fastener and movable relative to the head body,
    wherein the footing of the diaphragm is disposed between an inner side of a step surface of the annular step of the head body and an outer side of the annular protrusion, and directly contacts with the sound collecting surface of the head body at an annular circumference that is configured to move along the inner side of the step surface when the stethoscope head is in operation,
    wherein the diaphragm is configured to receive a high audio frequency in response to the diaphragm being pressed down and contacting the annular protrusion, and
    wherein the diaphragm is configured to receive a low audio frequency when not in contact with the annular protrusion.

11. The stethoscope head of claim 10, wherein an annular recess is provided on the sound collecting surface and formed in part by the inner side of the step surface of the annular step of the head body, and wherein the footing of the diaphragm is disposed in the annular recess.

12. The stethoscope head of claim 11, wherein the footing of the diaphragm contacts an inner side surface of the annular recess.

13. The stethoscope head of claim 10, wherein the annular step of the head body is disposed at an outer marginal part of the front side of the head body.

14. The stethoscope head of claim 10, wherein the footing of the diaphragm comprises an elastic material.

15. The stethoscope head of claim 10, wherein a back side of the head body is provided with graduations, wherein an outer side surface of the annular fastener is provided with an arrow, and wherein, when the annular fastener is screwed passively and the audio frequency is changed, the annular fastener is restorable to an original position according to the graduations marked by the arrow.

* * * * *